United States Patent [19]

Kutscher et al.

[11] Patent Number: 5,464,838
[45] Date of Patent: Nov. 7, 1995

[54] AMINOCARBOXYLIC ACID DERIVATIVES HAVING ANTIALLERGIC/ANTIASTHMATIC EFFECT AND A PROCESS FOR THEIR PREPARATION

[75] Inventors: Bernhard Kutscher, Maintal; Georg Niebch, Rodenbach; Ilona Fleischhauer, Offenbach; Jürgen Engel, Alzenau; Ute Achterrath-Tuckermann, Maintal; Stefan Szelenyi, Schwaig, all of Germany

[73] Assignee: Asta Medica Aktiengesellschaft, Dresden, Germany

[21] Appl. No.: 27,487

[22] Filed: Mar. 4, 1993

[30] Foreign Application Priority Data

Mar. 7, 1992 [DE] Germany ............... 42 07 234.4

[51] Int. Cl.⁶ .................. C07D 237/32; A61K 31/50
[52] U.S. Cl. .............. 514/248; 544/237; 560/38; 560/39
[58] Field of Search ............... 544/237; 514/248

[56] References Cited

U.S. PATENT DOCUMENTS

| 3,017,411 | 1/1962 | Ergelhrecht | 544/237 |
| 4,207,112 | 6/1980 | Ikenoue | 430/566 |
| 5,216,151 | 6/1993 | Murakami | 544/237 |

FOREIGN PATENT DOCUMENTS

| 0222191 | 10/1986 | European Pat. Off. |
| 0338444 | 4/1989 | European Pat. Off. |
| 1046625 | 8/1957 | Germany. |
| 2164058 | 1/1971 | Germany. |
| 3813531 | 5/1987 | Germany. |

OTHER PUBLICATIONS

Tatsumi, Hiroshima J Med Sci 33, 669 (1984).
Islam I, Ind. J. Chem 16B, 301 (1978).
Islam II, Ind. J. Chem 16B, 491 (1978).
Islam III, Indian J. Chem 16B, 593 (1978).

*Primary Examiner*—Mark L. Berch
*Attorney, Agent, or Firm*—Cushman Darby & Cushman

[57] ABSTRACT

6-amino carboxylic acid derivatives having antiasthmatic and antiallergic properties which can be used for the preparation of medicaments. The compounds have the formula:

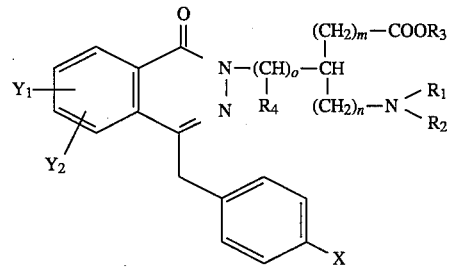

wherein $R_1$ and $R_2$ represent hydrogen, a straight-chain or branched alkyl radical with 1–6 carbon atoms, benzyl or phenylethyl, $R_3$ represents hydrogen, a straight-chain or branched alkyl radical with 1–6 carbon atoms or benzyl, X represents hydrogen, halogen, $C_1$–$C_6$-alkyl or $C_1$–$C_6$-alkoxy, $Y_1$ and $Y_2$ represent hydrogen, halogen, $C_1$–$C_6$-alkyl or $C_1$–$C_6$-alkoxy, where m, n and o can assume the values from 0–4.

4 Claims, No Drawings

AMINOCARBOXYLIC ACID DERIVATIVES HAVING ANTIALLERGIC/ANTIASTHMATIC EFFECT AND A PROCESS FOR THEIR PREPARATION

The present invention relates to

BACKGROUND OF THE INVENTION

In the form of 2-amino-substituted 6-amino caproic acid, the natural proteinaceous amino acid L-lysine is a compound which has varied physiological and biological effects. 6-amino-caproic acid is made on an industrial scale for various purposes, inter alia, prepared from ε-caprolactam.

SUMMARY OF THE INVENTION

The 6-aminocarboxylic acid derivatives of the invention are substituted in 3- or 4-position by benzyl-substituted phthalazinone radicals and are described by the following formula

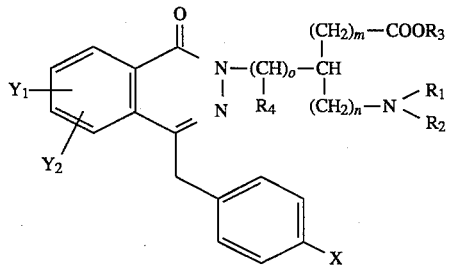

In the compound of Formula I $Y_1$, $Y_2$ represents hydrogen, halogen, for example fluorine or chlorine, $C_1$–$C_6$-alkyl, where the carbon chains may be straight or branched, $C_1$–$C_6$-alkoxy, $NO_2$, $NH_2$,

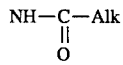

X represents hydrogen, halogen, for example fluorine or chlorine, $C_1$–$C_6$-alkyl, where the carbon chains may be straight or branched, $C_1$–$C_6$-alkoxy.

$R_1$ and $R_2$ may be the same or different, $R_1$ represents hydrogen, $C_1$–$C_6$-alkyl, straight-chain or branched, benzyl or phenylethyl. $R_2$ represents hydrogen, $C_1$–$C_6$-alkyl, straight-chain or branched, benzyl or phenylethyl.

$R_1$ and $R_2$ may also be joined together to form a carbocyclic ring having 5–7 ring members.

$R_3$ may represent hydrogen, a $C_1$–$C_6$-alkyl group where the carbon chain may be straight-chain or branched, or a benzyl group.

If $(m+n)=4$, new aminocaproic acid derivatives are involved.

$R_4$ may be hydrogen or $C_1$–$C_6$-alkyl, where the carbon chain may be straight-chained or branched.

m may assume the values from 0–4, n may assume the values from 0–4, o may also assume the values from 0–4.

The compounds of the invention are characterized by good antiallergic and antiasthmatic effect. Thus, the inhibitory effect ($ID_{50}$ values) in allergically induced bronchospasm in the guinea pig is 0.0099 mg/kg for the compound according to Example 3 and 0.0008 mg/kg for the compound according to Example 6.

The test model used to determine these values was a modification of the bronchospasmolysis experiment described by Konzett and Rössler (1).

The animals were narcoticized with urethane (1.5 g/kg i.p.). Trachea and v. jugularis were exposed by means of a skin incision. A tracheal cannula (Our own construction) was fitted to permit the intravenous application of propanolol, ovalbumin and a test substances, and which also permitted artificial respiration (Starling Pump, Braun Melsungen) and measurement of the intratracheal pressure (pressure uptake: Venous Pressure Transducer, Statham, type W 101 connected to a bridge amplifier, Hellige and Multicorder 6-channel ink plotter, Watanabe, type: WA 621-1). The entire preparation was completed after about 15 minutes. During the subsequent experiment the animals were ventilated with 40 breaths per minute and a volume of about 1 ml room air/100 g body weight. The intratracheal pressure was adjusted by this means to 10–15 cm water column. After a habituation phase of about 30 minutes, the test substances were administered intravenously. Propanolol was administered 10 minutes later. A bronchial constriction was triggered by injecting ovalbumin 15 minutes after intravenous application of the test substances. The resultant increase in intratracheal pressure was recorded on the plotter for at least 15 minutes.

In the model of the histamine-precontracted trachea (after R. W. Foster, J. Pharm. Pharmacol. 12, 189, 1960), the $IC_{50}$ value was 35.5 μMol/l for the compound of Example 6 and 3.86 μMol/l for the compound of Example 3.

The present invention also relates to a process for the preparation of the compounds of the invention. The process consists in building up correspondingly functionalized (in 3- or 4-position) aminocaproic acid derivatives (Formula III) or their protected or cyclized derivatives, and reacting with activated 4-benzyl-phthalazinones (Formula II).

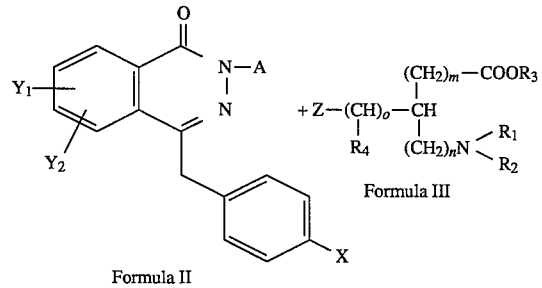

Formula II

Formula III

In Formulas II and III, X, Y1 and Y2 have the meanings given above.

A represents hydrogen.

$R_1$, $R_2$ and $R_3$ have the meanings given above.

Z can be hydroxy, halogen, mesylate or tosylate.

Solvents that may be used are for example polar aprotic solvents, such as dimethylformamide and dimethylacetamide as well as aliphatic and aromatic hydrocarbons such as toluene. Mixtures of the above-mentioned solvents may be used.

The reaction temperature is between −40° C. and 90° C., in particular between −5° C. and 50° C.

Proton acceptors may be metal hydrides, such as sodium hydride or alcoholates such as sodium ethylate or sodium methylate.

DETAILED DESCRIPTION OF PREFERRED EMBODIMENTS

The invention is illustrated in the following examples:

Example 1

4-(4-chlorobenzyl)-2-[5-(N-methyl-N-benzylamino)-1-carboxy-t-butyl-3-pentyl]-1(2H)-phthalazinone 3 g sodium hydride (80%, in white oil) are added to 21.6 g 4(4-chlorobenzyl)-1(2H)-phthalazinone in 200 ml dimethylacetamide (DMA) with cooling in an ice bath. 37 g 6-(N-methyl -N-benzylamino )-4-methylsulfonyloxy-caproic acid-t-butyl ester in 80 ml DMA are then added dropwise with cooling and stirring continued for 0.5 hour. The mixture is allowed to warm slowly—overnight—to room temperature and is then heated for 2 hours to 40° C.–50° C. The mixture is hydrolyzed by addition of 200 ml water with ice cooling. The precipitated oil is separated and dissolved in dichloromethane. After extraction twice with water, the organic phase is dried and concentrated. The residue is chromatographed over silica gel (Eluent: dichloromethane/methanol/ammonia 25% 95:4:1). 3.5 g are obtained (yellow oil).

The oxalate is formed in acetone for purposes of characterization:
(Melting point: 151°–153° C.)
$^1$H-NMR (d$_6$-DMSO, 500 MHz):=1.3 (s. 9H, t-Bu); 1.9–2.2 (m, 6H); 2.50 (s,3H,N—CH$_3$); 2.7 (m,1H); 2.95 (m, 1H); 4.05 (br.s,2H; 4.35 (dd, 2H); 5.05 (br. s, 1H); 7.2–7.4 (m, 9H); 7.8–8.05 (m,3H); 8.3 (m,1H); 11.3 (br.s,NH)

EXAMPLE 2

4-(4-Chlorobenzyl)-2-(5-methylamino-1-carboxymethyl-3-pentyl)-1(2H)-phthalazinone 37 g 4-(4-chlorobenzyl)-2-[5-(N-methyl-N-benzylamino)-1-carboxy-t-butyl-3-pentyl]-1(2H) -phthalazinone (Example 1) are dissolved in 200 ml 1,2-dichloroethane and mixed with 1.3 g 1–8-bisdimethylaminonaphthaline. 17.7 g chloroformic acid-1-chloroethylester are added dropwise over 20 minutes at 4°–8° C. The mixture is allowed to come up to room temperature and is then heated to boiling for 30 minutes. The solvent is substantially removed in a rotary evaporator and the residue is mixed with 100 ml methanol. The mixture is heated again for 2 hours under reflux, the solvent is removed and the residue taken up with water. The aqueous phase is extracted several times with dichloromethane. The combined organic phases are washed with dilute ammonia and water, dried and evaporated. The raw product is purified by chromatography over silica gel (eluent: dichloromethane/methanol/ammonia 25% 95:4:1).

Yield: 15.3 g oil
$^1$H-NMR (CDCl$_3$,500 MHz):=2.0–2.35 (m,6H); 2.4 (s, 3H, N-CH$_3$); 2.5–2.65 (m, 2H); 3.4 (br.s, 1H, NH); 3.6 (s, 3H,OCH$_3$); 4.3 (s, 2H, CH$_2$—Ph); 5.3 (m,1H); 7.15–7.35 (m,4H); 7.7 (m, 3H); 8.45 (m, 1H)

Treatment with methanol caused an ester interchange of the t-butyl into the methyl ester.

Example 3

4-(4-chlorobenzyl)-2-(5-methylamino-1-carboxy-3-pentyl)1(2H) -phthalazinone 15 g 4-(4-chlorobenzyl)-2-(5-methylamino-1-carboxymethyl-3-pentyl) 1(2H)-phthalazinone (Example 2) are dissolved in 150 ml methanol and reacted with 21 ml 5M sodium hydroxide solution. The solution is heated for 1.5 hours to 50° C., then concentrated in a rotary evaporator, and the residue reacted is with 105 ml 1M HCl (pH 6). The aqueous solution is first shaken with diethylether to remove nonpolar impurities and then extracted with dichloromethane. The combined dichloromethane phases are concentrated, and the raw product is crystallized from ethanol. The crystalline product is precipitated absorptively with ether and dried in a vacuum (55° C./2 Torr).

Yield: 9.42 g
Melting point: 132° C.

Example 4

4-(4-chlorobenzyl)-2-[5-(N-methyl-N-benzylamino-1-carboxymethyl-2-pentyl]-1(2H)-phthalazinone 10.8 g 4-(4-chlorobenzyl)-1(2H)-phthalazinone in 90 ml DMF are added dropwise with cooling in an ice bath to a suspension of 1.26 g sodium hydride (80% in white oil) in 20 ml dimethylformamide (DMF). The solution of 11.5 g 6-(N-methyl-N-benzylamino)-3-methylsulfonyloxy-caproic acid methyl ester in 70 ml DMF are then added thereto, also with cooling. Stirring is continued and the solution is slowly allowed to come up to room temperature. When the reaction is completed (approx. 24 hours) excess of sodium hydride is destroyed by adding water dropwise with cooling in an ice bath. The mixture is then poured onto ice water and extracted several times with t-butylmethylether.

The combined organic phases are dried and concentrated. The raw product is chromatographed over silica gel. (Eluens: dichloromethane/methanol/ammonia 25% 95:4:1) .

The yield is 7.9 g (oil).
$^1$H-NMR (CDCl$_3$, 500 MHz):=1.4 (m, 1H; 1.55 (m,1H); 1.8 (m, 1H);2.0 (m, 1H); 2.1 (s,3H,N—CH$_3$); 2.4 (m, 2H, CH$_2$C=O); 2.7 (m, 1H, N—CH; 3.0 (m,1H, N—CH); 3.4 (m, 2H; N—CH$_2$—Ph); 3–6 (s,3H, OCH$_3$); 4.25 (br.s, 2H, CH$_2$Ph); 5.6 (m, 3H); 8.5 (m, 1H)

Example 5

4-(4-chlorobenzyl)-2-(5-methylamino-1-carboxymethyl-2pentyl)-1(2H)-phthalazinone The reaction is carried out as described in Example 2 starting from 6.9 g 4-(4-chlorobenzyl)2-[5(N-methyl-N-benzylamino)-1-carboxymethyl-2-pentyl]-1(2H)-phthalazinone (Example 4).

Yield: 4.4 g

Example 6

4-(4-chlorobenzyl)-2-[5-methylamino-1-carboxy-t-2-pentyl]- 1(2H) -phthalazinone

The compound is prepared in an analogous matter to Example 3 starting from 4.3 g 4-(4-chlorobenzyl)-2-(5-methylamino-1-carboxymethyl-2-pentyl]-1(2H)-phthalazinone (Example 5) by alkaline hydrolysis with dilute NaOH.

Yield: 3.0 g
Melting point: 186°–189° C.

Example 7

4-(4-fluorobenzyl)-2-[5-(N-benzyl-N-phenylethylamino)-1-(carboxy-2-propyl)-3-pentyl]-1(2H)-phthalazinone 5.7 g methanesulfonic acid chloride in 20 ml dichloromethane are slowly added dropwise with cooling in an ice bath to a solution of 15.7 g 6-(N-benzyl-N-phenylethylamino)- 4-hydroxycaproic acid-2-propylester and 5.0 g triethylamine in 80 ml dichloromethane. The mixture is stirred for a further approx. 1.5 hours in an ice bath, any precipitated triethylammonium chloride is suction filtered and the solution is washed twice with saturated sodium hydrogen carbonate solution as well as once with saturated common salt solution. The organic phase is dried and concentrated. The mesylate accumulates as an oily precipitate which is diluted without further cleaning with 40 ml dimethylacetamide (DMA) and added dropwise to the solution of 5.6 g 4-(4-fluorobenzyl)-1(2H)- phthalazinone and 0.75 g sodium hydride (80%, in white oil) in 80 ml DMA, cooled to approx. 5° C. The reaction mixture is allowed to come up to room temperature and stirring is then continued for a further 5 hours at 50°–60° C.

For purposes of hydrolysis, water is slowly added dropwise with cooling in an ice bath and the mixture is then extracted three times with dichloromethane. The combined organic phases are dried and concentrated. The remaining oil is chromatographed over silica gel (Eluens: dichloromethane/methanol/ammonia 25% 95:4:1).

Yield: 10.8 g

Example 8

4-(4-fluorobenzyl)-2-[5-(N-phenylethylamino)-1-(carboxy-2-propyl)-3-pentyl]-1(2H) -phthalazinone 10.5 g 4-(Fluorobenzyl)-2-[5-(N-benzyl-N-phenylethylamino)-1-carboxy-2-propyl-3-pentyl]-1(2H)-phthalazinone (Example 7) are reacted in a manner analogous with Example 2 in 100 ml 1,2-dichloroethane with 6.86 1.8-bisdimethylaminonaphthaline and 4.58 g chloroformic acid-1-chloroethylester. Working up is as described in Example 2. The raw product is chromatographed twice.

Yield: 1.9 g

Example 9

4-[4-Fluorobenzyl)-2-[5-(N-phenylethylamino)-1-carboxy-3-pentyl]-1(2H)-phthalazinone 1.7 g of the 2-propylester of Example 8 are hydrolyzed with dilute sodium hydroxide solution in a manner analogous with Example 3. After acidification with aqueous HCl (pH 5–6) and drying, 1.0 g of the product is obtained.

Melting point: 190°–191° C.

What is claimed is:

1. Compounds having the structure of formula I,

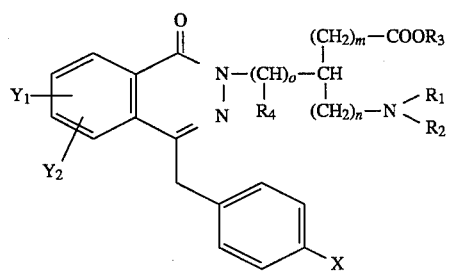

where $R_1$ and $R_2$ are the same or different and represent hydrogen, a straight-chain or branched alkyl radical with 1–6 carbon atoms, benzyl or phenylethyl, $R_3$ represents hydrogen, a straight-chain or branched alkyl radical with 1–6 carbon atoms or benzyl, X represents hydrogen, halogen, $C_1$–$C_6$-alkyl or $C_1$–$C_6$-alkoxyl.

$Y_1$ and $Y_2$ are the same or different and represent hydrogen, halogen, alkyl with 1–6 carbon atoms or alkoxy with 1–6 carbon atoms, where m, n and o can assume the values from 0–4.

2. Compounds according to claim 1, in which $R_1$, $R_2$ and $R_3$ represent hydrogen, alkyl with 1–6 carbon atoms, benzyl or phenylethyl, X represents chlorine or fluorine and $Y_1$ and $Y_2$ represents hydrogen.

3. Pharmaceutical compositions comprising an antiallergic/antiasthmatic effective amount of at least one compound according to claim 1 or their pharmaceutically acceptable salts, together with a pharmaceutically acceptable carrier therefor.

4. A method of treating allergies, inflammations and asthma which comprises administering to a patient suffering therefrom with the pharmaceutical composition as set forth in claim 3.

* * * * *